(12) United States Patent
Fleming et al.

(10) Patent No.: US 6,925,882 B1
(45) Date of Patent: Aug. 9, 2005

(54) METHODS FOR ULTRASONIC INSPECTION OF SPOT AND SEAM RESISTANCE WELDS IN METALLIC SHEETS

(76) Inventors: Marvin F. Fleming, 1480 Montclaire Pl., Los Altos, CA (US) 94024; Jack P. Clark, 107 Cappy Ct., San Jose, CA (US) 95111

( * ) Notice: Subject to any disclaimer, the term of this patent is extended or adjusted under 35 U.S.C. 154(b) by 0 days.

(21) Appl. No.: 10/267,140

(22) Filed: Oct. 7, 2002

Related U.S. Application Data (60) Provisional application No. 60/327,374, filed on Oct. 5, 2001.

(51) Int. Cl.[7] ............................................ G01N 29/04
(52) U.S. Cl. ......................................... 73/632; 73/635
(58) Field of Search ....................... 73/642, 632, 644, 73/636, 635, 639

(56) References Cited

U.S. PATENT DOCUMENTS

| | | | | |
|---|---|---|---|---|
| 3,832,889 | A | * | 9/1974 | Bauer ........................... 73/642 |
| 4,208,917 | A | * | 6/1980 | Aoyama et al. ............... 73/644 |
| 4,454,764 | A | * | 6/1984 | Sorenson ....................... 73/642 |
| 5,228,343 | A | * | 7/1993 | Schoenen et al. ............. 73/644 |
| 5,473,943 | A | * | 12/1995 | Schoenen et al. ............. 73/644 |
| 5,537,875 | A | * | 7/1996 | Viehmann et al. ............ 73/588 |
| 5,804,730 | A | * | 9/1998 | Pfannenstiel et al. ......... 73/622 |
| 5,814,731 | A | * | 9/1998 | Alexander et al. ............ 73/644 |
| 5,952,577 | A | * | 9/1999 | Passi ............................. 73/618 |
| 6,072,144 | A | * | 6/2000 | Perryman ..................... 219/109 |
| 6,532,820 | B1 | * | 3/2003 | Fleming et al. ............... 73/627 |

FOREIGN PATENT DOCUMENTS

| | | | | |
|---|---|---|---|---|
| EP | 833151 | A2 * | 4/1998 | .......... G01N 29/10 |
| JP | 61223648 | A * | 10/1986 | .......... G01N 29/04 |
| WO | WO 00/40960 | * | 7/2000 | .......... G01N 29/00 |

* cited by examiner

*Primary Examiner*—Hezron Williams
*Assistant Examiner*—Rose M. Miller
(74) *Attorney, Agent, or Firm*—Allston L. Jones (57) ABSTRACT

Spot and seam weldments in sheet metal components are inspected by a method in which a focused ultrasonic beam is directed into the weldment from the outside surface together with measuring the motion of the ultrasonic beam over the weldment. Reflected ultrasonic waves are received and signals indicative thereof are produced and processed or displayed as image forms that are easily recognized by an operator. This data is displayed as an A-Scan where a predetermined time window is established on the display, based on the time-of-flight difference between the outer surface, the weld interface or interfaces and the inner or opposite surface of the component. Certain ultrasonic signals are indicative of the degree of complete fusion in the weld zone and provide data relative to the total fused thickness and to defects either in the sheet metal or in the weld.

9 Claims, 8 Drawing Sheets

METHODS FOR ULTRASONIC INSPECTION OF SPOT AND SEAM RESISTANCE WELDS IN METALLIC SHEETS

This application claims the benefit of Provisional Application Ser. No. 60/327,374 filed Oct. 5, 2001.

BACKGROUND OF THE INVENTION

1. Field of the Invention

This invention relates to a method of inspecting the integrity of spot and seam welds and more particularly it relates to an ultrasonic, nondestructive method of inspecting spot and seam welds.

2. Description of the Prior Art

Heretofore, the inspection of spot and seam welds has been performed using visual, radiographic and ultrasonic methods; as described in the Metals Handbook (Metals Handbook, 9th Edition, Volume 17, "Nondestructive Evaluation and Quality Control", ASM International, Metals Park, Ohio, September, 1989, pg. 335) and the Nondestructive Testing Handbook (Nondestructive Testing Handbook, 2nd Edition, Volume 7. "Ultrasonic Testing", American Society for Nondestructive Testing, Columbus, Ohio, 1991, pgs. 10–12 and pgs. 557–566). The visual and radiographic methods reveal little or nothing concerning the fusion of these welds. The prior art ultrasonic method referred to in the literature is a pulse-echo method however is generally referred to as a ring down technique throughout the industry. It makes use of the reflected amplitude and the envelope formed in time by many multiple reflections. Basically an envelope of these reflections are used to indicate if the weld is fused or not. Destructive sampling techniques of welds have also been in use. This has been done by either separating the sheets with a chisel or with a tensile pull technique. Another destructive technique in common use cuts through the weldment, polishes and enhances the weldment so that the dimensions of the fused part of the weld can be measured optically. In this prior art, the dimensions of the weld are used to infer the weld quality. Because the ultrasonic method can penetrate a fused weld zone, the length of continuous fused section(s) can be measured and easily related to weld strength. Additionally, ultrasound is sensitive to common weld defects.

It would be advantageous to have a technique and system that includes the capability to accurately measure dimensions of fusion in the weldment and to determine the presence of weld defects. Using the dimensions of the fused sections as a quality indicator would make the ultrasonic process highly reliable and accurate and save on industrial injury which sometimes occurs during the expensive destructive quality tests of welds. The present invention provides such a technique and system.

SUMMARY OF THE INVENTION

Spot and seam weldments in sheet metal components are inspected by a method in which a focused ultrasonic beam is directed into the weldment from the outside surface together with a means for measuring the motion of the ultrasonic beam over the weldment. Reflected ultrasonic waves are received and signals indicative thereof are produced and processed or displayed as image forms that are easily recognized by an operator. This data is displayed as an A-Scan where a predetermined time window is established on the display, based on the time-of-flight difference between the outer surface, the weld interface or interfaces and the inner or opposite surface of the component. Certain ultrasonic signals are indicative of the degree of complete fusion in the weld zone and provide data relative to the total fused thickness and to defects either in the sheet metal or in the weld.

A manual scanner is used to move the ultrasonic transducer in a predetermined scanning motion on the surface of the part. This transducer both generates the transmitted waves and receives the reflected waves from the weldment coupling of the transducer to the component is achieved via a continuous fluid filed column. Encoder readings are received from the scanner, which provides dimensional data, relating the position of the transducer on the surface of the part. By combining the ultrasonic and the encoder data, B- and C-Scan images (cross sectional and plan views) of the component are generated and displayed. These images are easily used to determine the quality of the weldment in question. These displays are then used to measure the diameter of spot welds, the distance between spot welds, the length and widths of seam welds plus the size, shape and location of defects, such as porosity or lack of fusion, within the weldments, plus laminar type defects, either in the base material or the weld zones.

DETAILED DESCRIPTION OF THE INVENTION

Figure 1:
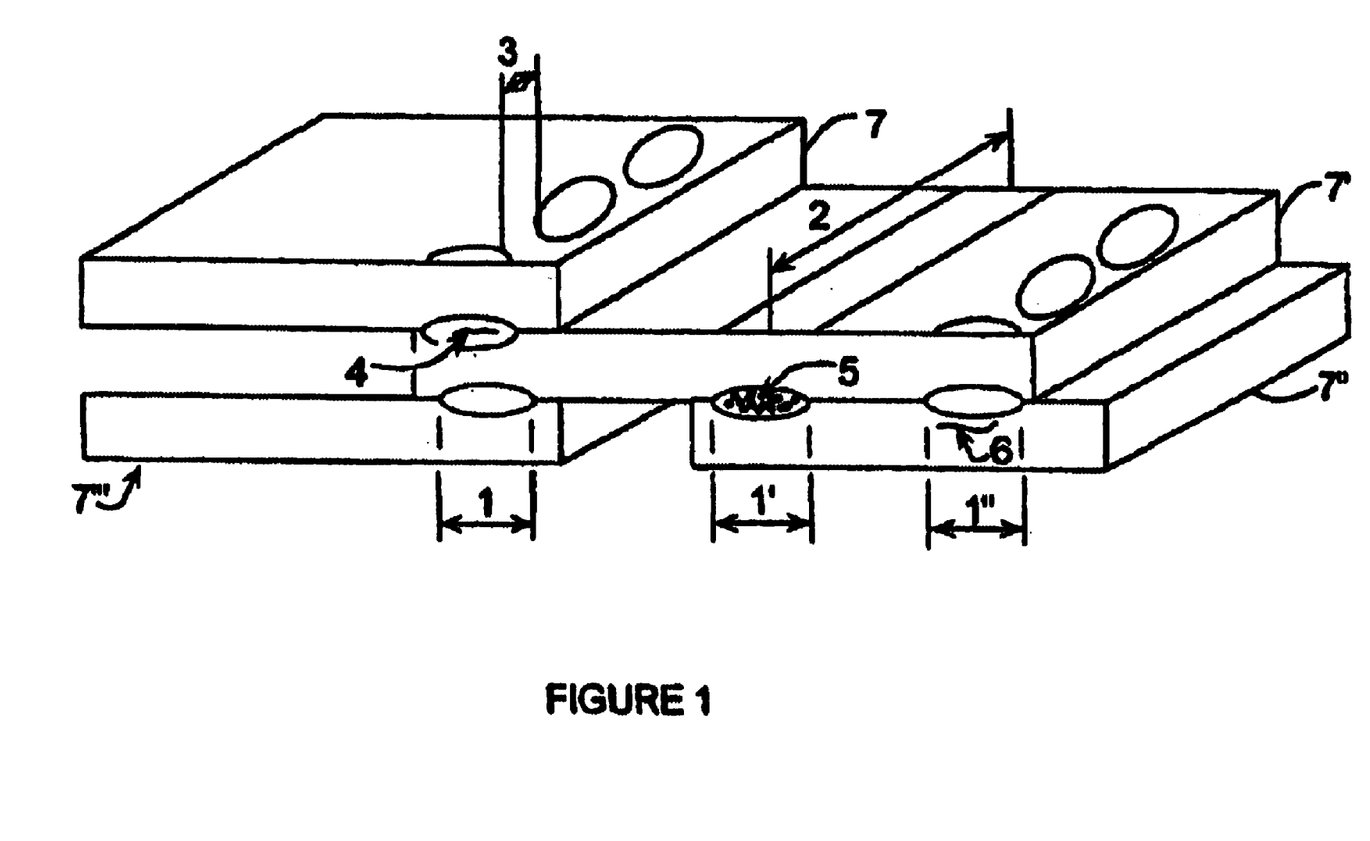
FIG. 1 is a perspective view of four metal plates that overlap various of each other to illustrate typical spot and seal welds.

The present invention uses a focused ultrasonic beam with an encoder of the transducer movement to measure the length and penetration of a fused weldment using an ultrasonic transducer that has been selected to have a frequency that will be transmitted by properly fused weldments and blocked by weldment defects. The focused beam is also used to measure critical lengths of fusion in both spot and seam welds as shown in FIG. 1. The dimensions labeled 1, 1', 1" represent the width of fusion zones of seam welds, 3 represents the distance between spot welds and 2 represents the length of the seam weld depicted, the welds being made in the welded plates 7, 7', 7" depicted in FIG. 1. Defect dimensions and location are also measured by the present invention; such as those illustrated as weld lack of fusion 4, porosity 5 and laminar defects 6 as illustrated in FIG. 1.

Spot and seam weld(s) of the types illustrated in FIG. 1 are normally used to fuse two or more sections of sheet metal together. As such they can be considered as a lap type of joint. They are produced by placing electrodes directly in line with each other in contact with opposing surfaces of the sheets to be fused. A predetermined amount of pressure is applied to assure good contact of the electrodes with the metallic surfaces and good contact between the surfaces to be joined. An electrical current is then passed from one electrode to the other flowing through the sheets of metal generating heat in the metal. The proper combination of heat and applied pressure results in the surfaces of the sheets being welded or fused together. Normally the position of such welds can only be seen visually due to a slight surface depression caused by the pressure of the electrodes and possibly by some discoloration due to the heat. Naturally the size of the actual fusion zone is critical to the integrity of the component as is the detection of defects which could jeopardize the integrity of the weld itself. Such defects include lack of fusion within the weld zone, porosity and laminar type defects, either in the weld, or in the base material of the sheets adjacent to the fused areas. As for a series of spot welds the distance between the fused zones of the welds can have a direct effect on the overall strength of the welded component.

All of these quality related features can be detected, measured and evaluated using the present invention. FIG. 1 is a diagram showing the different type of resistant weld configurations and include illustrations of defects such as the lack of fusion in a weld and plate laminations adjacent to a weld edge. The dimensions of interest in determining weld strength can be measured; such as the length of the fusion zones of spot welds, the distance between spot welds plus the length and width of seam welds. To accomplish this, a beam of ultrasound (typically 5–15 MHz.) is directed into the sheets just above the area of fusion.

The spot and seam type welds used to attach two or more sheets of metal are addressed; as shown in FIGS. 1–7 where the measurement of fused weldment dimensions is one of the objectives of the present invention.

Figure 2:
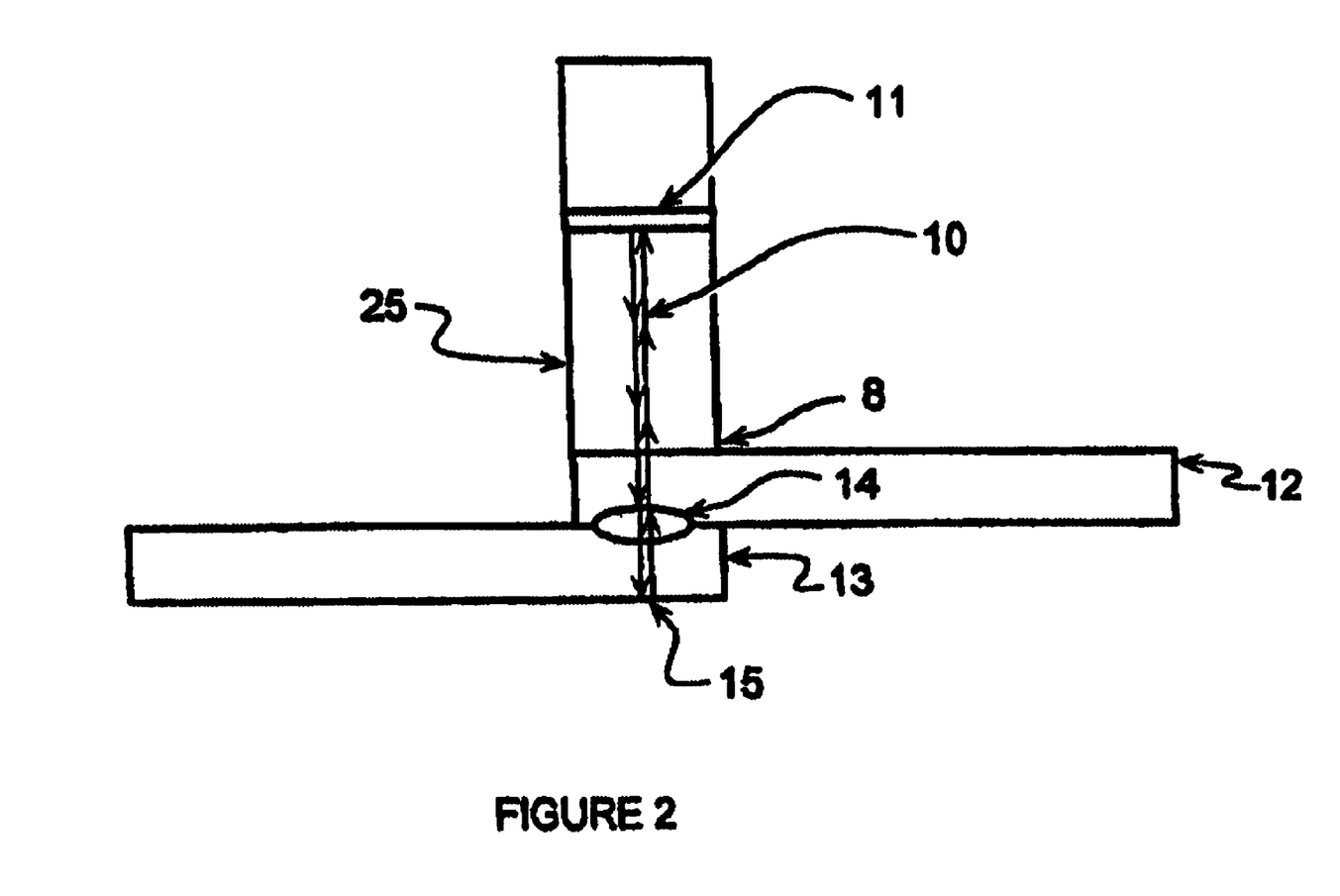
FIG. 2 is a simplified side plan view of the transducer and liquid column of the present invention showing ultrasonic propagation to and from the metal plates and the weld.

FIG. 2 is a simplified diagram of the propagation of an ultrasonic beam 10 produced by transducer 11, through a liquid column 25 (typically water filled), to a weld or fusion zone 14 between upper plate 12 and lower plate 13. In this view, a forward directed portion of ultrasonic beam 10 is shown being reflected from the far-side 15 of plate 13 as a returning portion of beam 10 indicating that the weld 14 is complete. As transducer 11 is moved relative to the surface of plate 12 above a location where there is no fusion zone between plates 12 and 13, or where weld 14 is poor, ultrasonic beam 10 will be reflected from the far-side of plate 12, instead of from the far side point 15 of plate 13.

FIG. 2 illustrates the transducer 11 location with respect to a weld 14 plus the orientation of the ultrasound beam and the propagation of the ultrasound beam 10 through the weldment. The sound 10 passes through the wall of the entry sheet 12 and into the fusion zone 14. If fusion has occurred (i.e., weld 14 is a good weld) the sound will pass through the weldment 14 and through the near wall of bottom sheet 13. In that situation the ultrasonic beam 10 will be reflected back to the transducer 11 from the far surface 15 of sheet 13 (in the case where two or more sheets may be joined together—sometimes referred to as lap welded). If fusion has not occurred or a lack of fusion exists or some other discontinuity is present (i.e., a poor or incomplete weld), the sound beam 10 will not pass through fusion zone 14 and will instead be reflected back to transducer 11 from the far side of sheet 12 instead of side 15 of sheet 13 as discussed above for a good weld, where it will be detected.

FIG. 1 shows examples of three common weld discontinuity, or defect, 4, 5 and 6. Since the velocity of sound in the particular metal has been predetermined and is known, the time of flight of the ultrasonic beam in the material can be directly related to the distance the beam has traveled to reach and return from a reflector. In the case of two or more sheets that have been successfully fused together, that distance will be the total combined thicknesses of all of the sheets; if there is no fusion zone or if the fusion is incomplete the distance traveled will be much less. All of this data is processed by a data acquisition system to generate commonly used displays (Nondestructive Testing Handbook, Volume II. Edited by the Society for Nondestructive Testing, Ronald Press, NY 1963, pgs 43.34 through 43.36). It can be displayed as amplitude (intensity) vs. time on an oscilloscope type display both in real time or at some convenient later time using data storage techniques.

Figure 3:
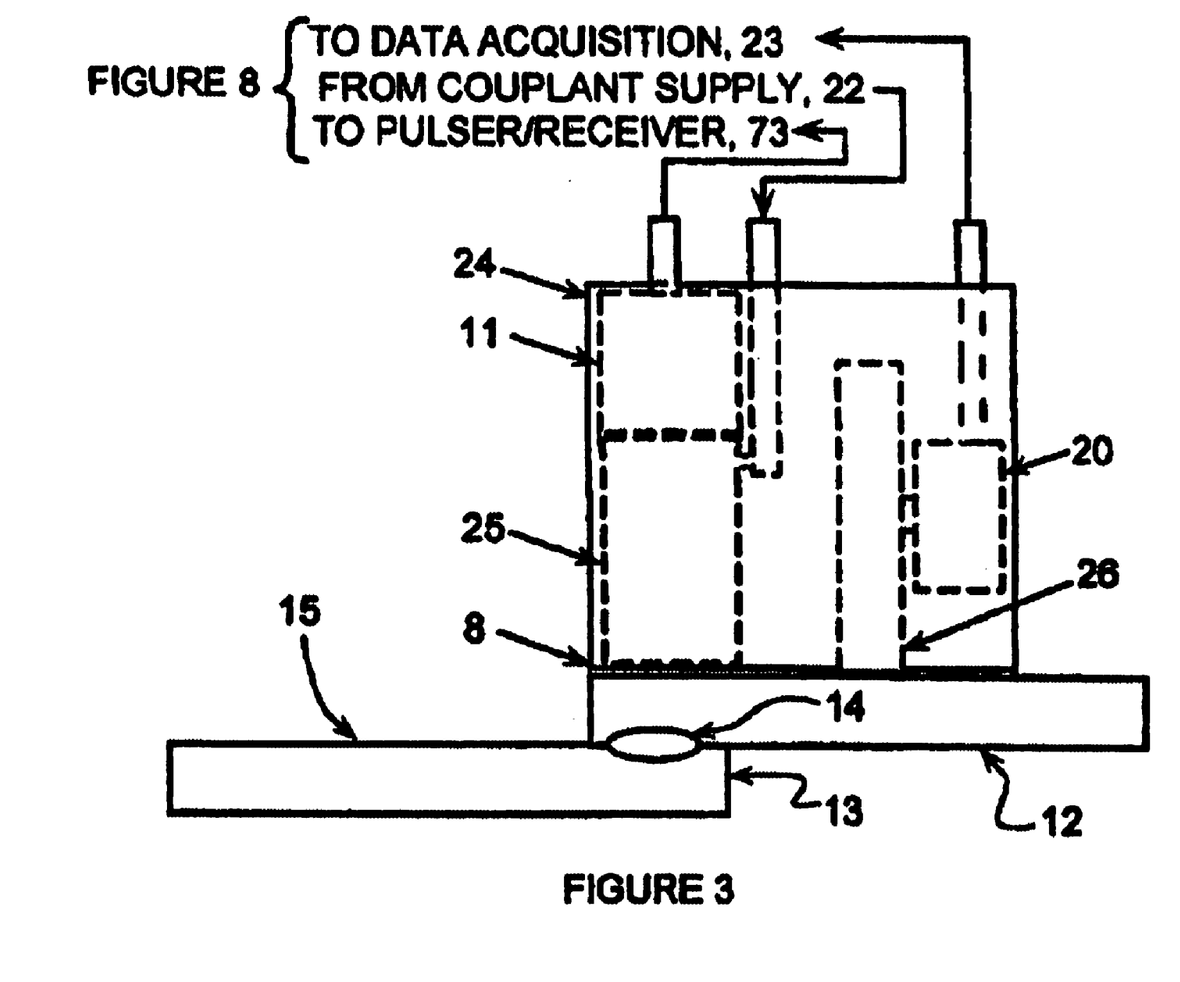
FIG. 3 is similar to FIG. 2 with details of a transducer scanner added to show the scanner position with respect to the weld.

FIG. 3 adds a scanner 24 and related elements to the diagram of FIG. 2. Here the scanner housing is shown enclosing transducer 11 and liquid column 25, as well as traction wheel 26 with encoder 20 connected to the center axis thereof. As scanner 24 is moved, wheel 26 rolls along the top surface of plate 12 with that rotation converted to distance traveled by encoder 20, which provides position information when the starting point of the scan is known and thus the location of transducer 11 with respect to weld 14. The combination of the encoder 20, transducer 11, and ancillary couplant supply 22 (FIG. 8), and data acquisition cables 23 (FIG. 8) are typically housed as an assembly called a scanner housing 24. A scanner consisting of a housing containing a focused ultrasonic transducer with a standoff element usually consisting of a liquid column 25 is shown.

Using a typical position encoder 20 to measure the relative location of the ultrasonic transducer 11 accomplishes the acquisition of the essential ultrasonic data related to weldment dimensions in front of and behind the plane depicted in FIG. 3.

In FIG. 3 transducer 11 is focused so the focal zone includes the working depth of the welds of interest. The encoder 20, is driven directly by an attached traction wheel 26 which, for example, rotates on the surface of a component plate. Normally the scanner is hand held and scanning is performed manually; however, the scanner could also be transported by a motor driven scanning mechanism (not shown). The method of encoding in both orthogonal directions over the surface of the weldment is known in the art. Liquid column 25 is used with the couplant supply to maintain ultrasonic coupling contact with the inspection surface (e.g., top side of plate 12). The water wets the surface for ultrasonic coupling. In some cases, particularly when using larger diameter transducers on uneven or distorted surfaces, a flexible membrane may be added to the contact surface of the scanner, so that the bottom of the liquid column takes the shape of the distorted surface and good coupling is maintained. The flow of water from a hole is minimized and is continually replaced by a couplant supply sub-system. The scanner is manually placed on the surface of the component to be inspected and moved in approximately straight lines over the weldments. Movement of the scanner turns the traction wheel, which is in contact with the surface of the component.

The ultrasonic probe of FIGS. 2 and 3 includes a narrow tip 8 at the bottom of water column 25 that is disposed to engage the component to be tested. So configured, ultrasonic transducer 11 directs a signal through water column 25 to, and through, narrow tip 8 and the couplant wetting the top surface of sheet 12 to the point of inspection and receives the return signal from the point of inspection through the same path in reverse order. As such, narrow tip 8 of the housing defines a bearing surface that is disposed to engage the component to be tested. Additionally, tip 8 can be made interchangeable and in different sizes to compliment various weld sizes that might be encountered, as well as in several different configurations to provide various bearing surfaces, i.e., conventional bearing or slide. With the various sizes and bearing surface of tip 8 available, the ultrasonic probe of the present invention has the ability to complement various the welds for inspection.

Figure 4:
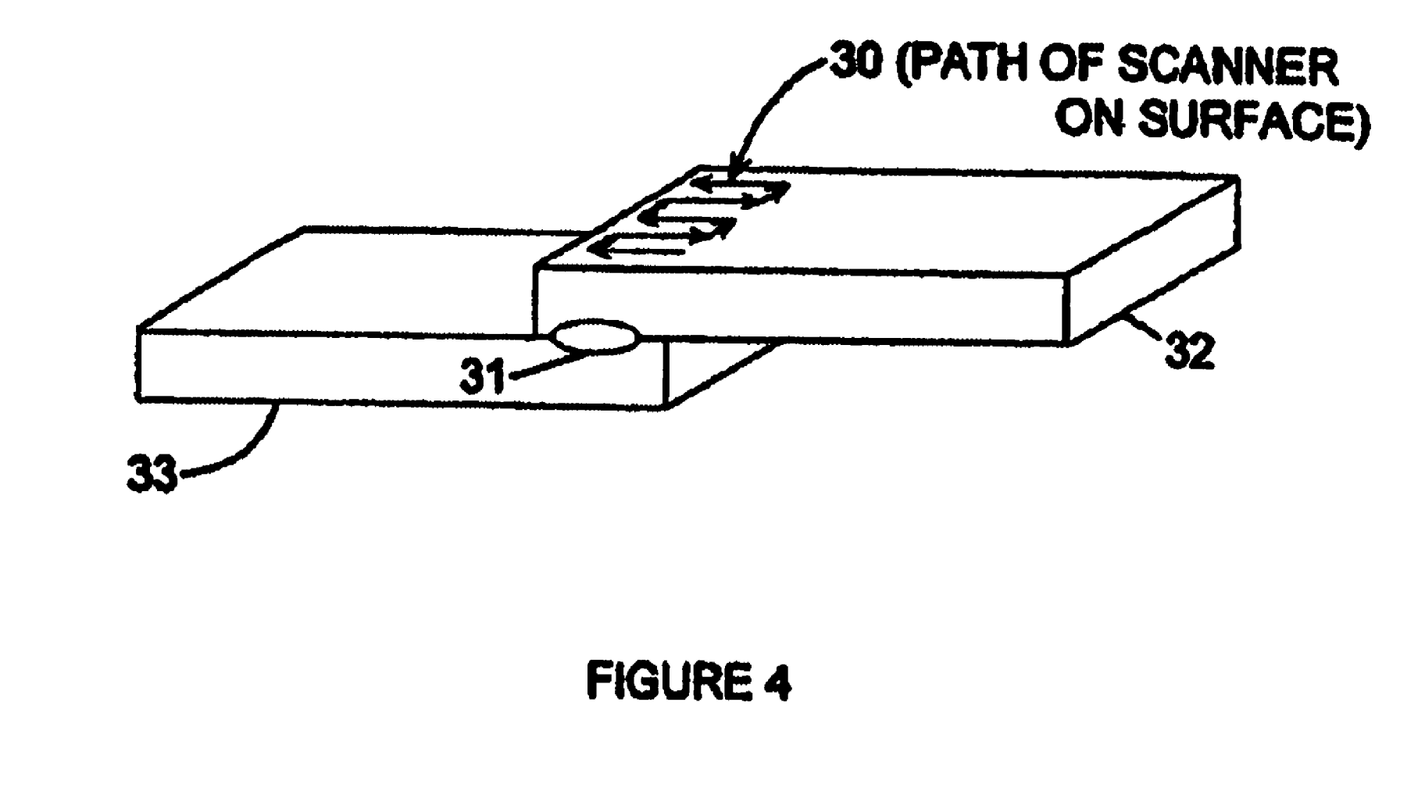
FIG. 4 illustrates a combination x and y axis scan pattern on the surface of a first plate at the location of a seam weld with a second plate.

FIG. 4 is a sketch illustrating the scanning pattern 30 used to obtain a C-Scan of the weldment 31 attaching two plates 32 and 33 and undergoing inspection. The prior art contains several means for evaluating the weld dimensions from the ultrasonic data such as commonly referred to as A-scans, B-scans and C-scans. In order to collect a proper B-scan the operator must use the same judgment for positioning the ultrasonic beam as used in positioning the weldment cuts for the destructive evaluations. A raster scan eliminates the need for accurate positioning of the B-scan by employing the C-scan ultrasonic techniques. This is especially useful when evaluating a seam weld as shown in FIG. 4.

Figure 5A:
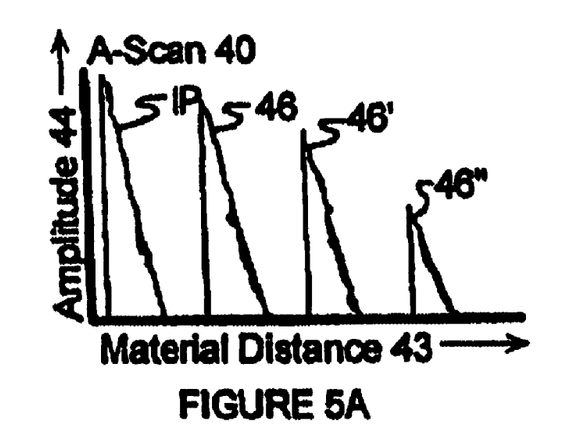
FIGS. 5A–5C illustrate typical A-Scans for three sheets wieded together where there is lack of fusion between sheets 1 and 2, full fusion between sheets 1 and 2 and lack of fusion between sheets 2 and 3, and full fusion between each of the adjacent sheets, respectfully, to evaluate spot and seam weldments.
Figure 5B:
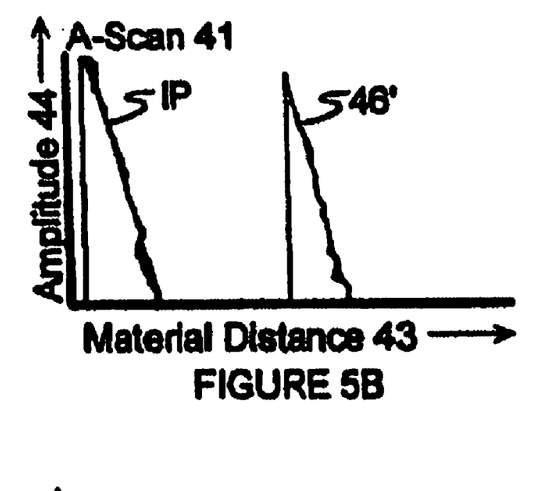
Figure 5C:
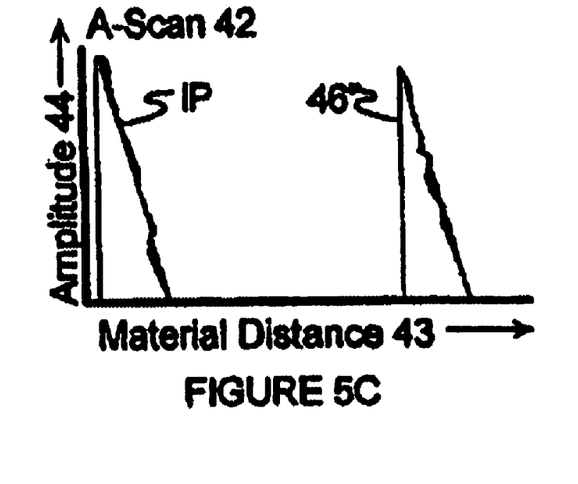

FIGS. 5A–5C illustrates three oscilloscope displays (A-Scan) of reflected ultrasonic signals from different reflectors associated with the welds, as shown in FIG. 1. The horizontal axis of each A-scan is calibrated in time lapse after the initial pulse IP or distance 43 into the material and the vertical axis is calibrated in amplitude 44 of the signals. In FIG. 5A A-scan 40 (upper left) shows reflections that correspond to an interval of one thickness for plate 7 in FIG. 1. In FIG. 5B A-scan 41 (upper right) shows the A-scan for a point on the plate where there is a full fusion existing between plates 7 and 7'. In FIG. 5C A-scan 41 may also represent another situation where there is a lack of fusion between plates 7' and 7" (for the case where three plates are to be welded). A-scan 42 (bottom center) shows the A-scan at a point where there is full fusion existing between plates 7, 7' and 7".

Figure 6A:
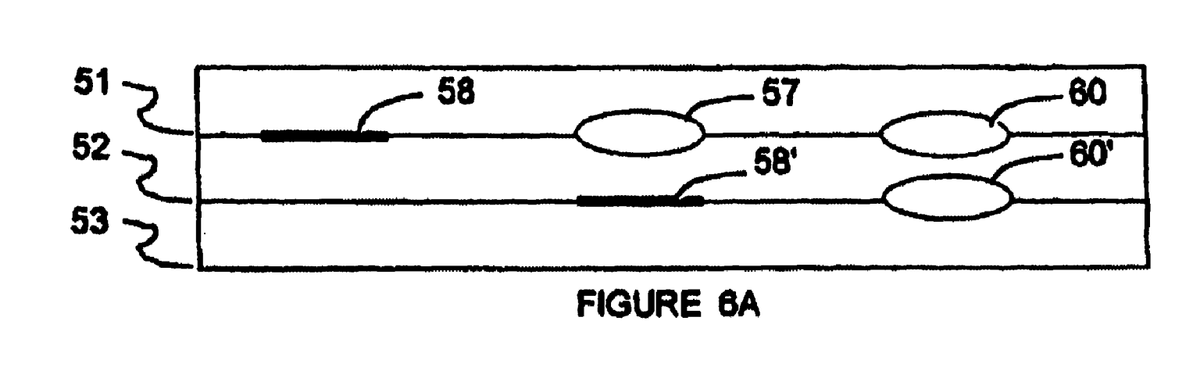
FIG. 6A is a vertical slice through three sheets of metal illustrating locations of various fusions and non-fusions between adjacent sheets.
Figure 6B:
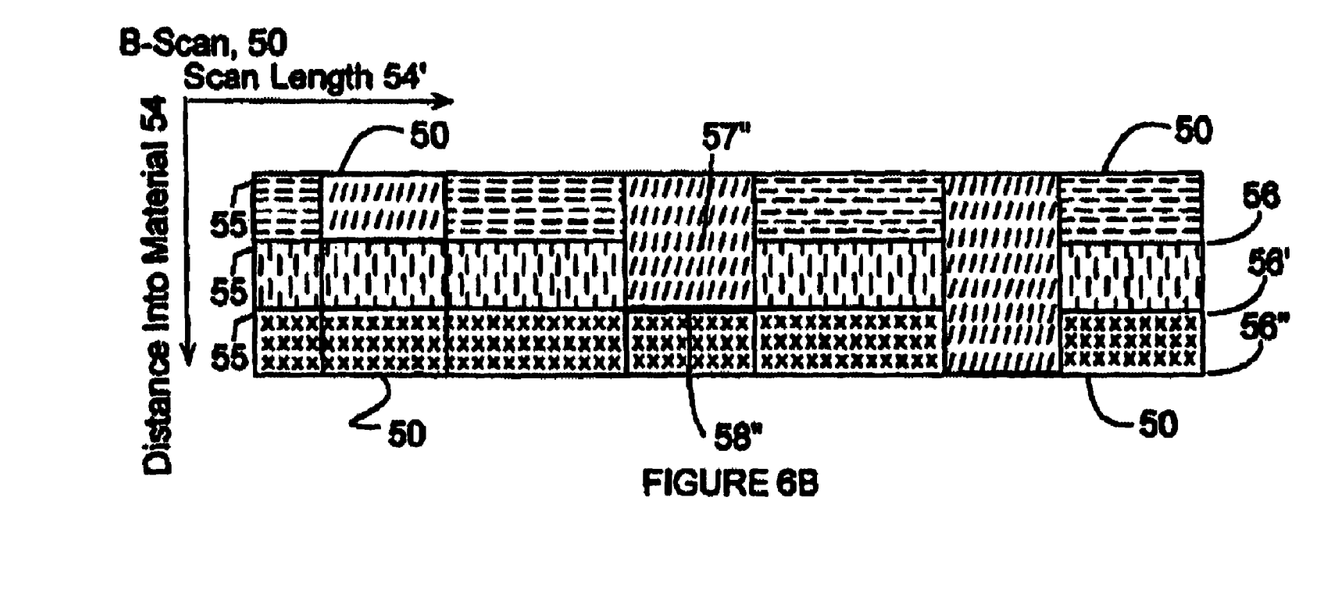
FIG. 6B illustrates typical B-Scans for the three sheets as shown in FIG. 6A to evaluate spot and seam weldments.

FIG. 6B illustrates a cross-sectional image B-Scan 50 (B-Scan 50 [Metals Handbook, 9th Edition, Volume 17, "Nondestructive Evaluation and Quality Control", ASM International, Metals Park, Ohio, September, 1989, pg. 335; Nondestructive Testing Handbook, Volume II, Edited by the Society for Nondestructive Testing, Ronald Press, NY 1963, pgs 43.34 through 43.36]) below the cross section of weldments shown in FIG. 6A which have been inspected. The use of the B-scan is useful for making a recordable image of the quality of the weldment. Continuous or digitization and storage of ultrasonic data (FIGS. 5A–5C) and positional encoder data (FIG. 3) are combined to plot the image. The horizontal axis of plot 50 is the length traveled along the surface of the component (scan length 54') and the vertical axis is the time of flight 54 (time of flight 54 is equated to distance into the material, i.e., below the surface of the top plate 51) of the ultrasonic signals from the reflectors encountered. The amplitude of the ultrasonic signals can also be displayed using a color code or a grey scale 55 (since a grey scale does not reproduce well, three different fills are used to show various conditions). The top layer of the B-scan is shown with horizontal broken lines; the middle layer is shown with vertical broken lines, and the bottom layer is shown with "x"s. In the areas where there an attempted weld has been scanned diagonal hash marks are used to illustrate the depth to which the ultrasonic signal penetrated before being reflected back to the scanner. The location of the transition amplitude peaks 46 and 46' from the A-scans of FIGS. 5A–5C correspond to the gray scale transitions 56, 56' and 56" in FIG. 6B. The lack of fusion in region 58 of FIG. 6A is revealed by the presence of the 56 interface where 58 is located. The absence of the interface 56 in the area of fusion 57 as shown in FIG. 6A indicates the presence of good quality fusion. The width of the weld image 57" is directly related to the width of the fusion in the weld 57. The lack of fusion 58' located between sheet 2 and sheet 3 (see FIG. 6A) results in an interface line 56' in the B-scan image 50 in the area 58" and corresponds to the return 46' in A-scan 41 of FIG. 5B. Full fusion of the plates at 60 and 60' in FIG. 6A produces no transition in the B-scan image at levels corresponding to the 56 and the 56' transitions however it does produce a transition at level 56" below the fusion for welds 60 and 60'. The A-scan 42 of FIG. 5C produced when the ultrasonic transducer is over welds 60 and 60' sows a response at 46". The width of the B-scan image corresponds to the width common to welds 60 and 60' and the corresponding quality of the weld.

Figure 7A:
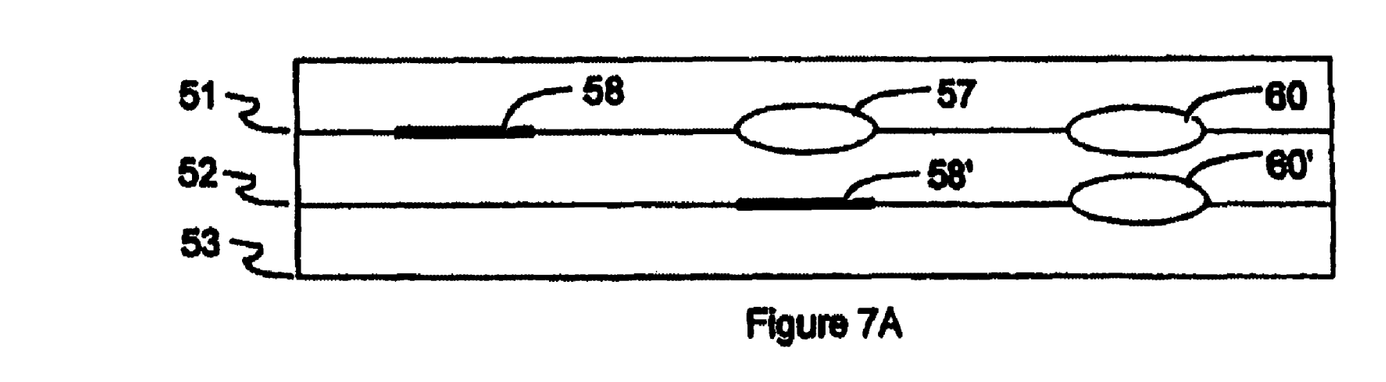
FIG. 7A is the same as FIG. 6A.
Figure 7B:
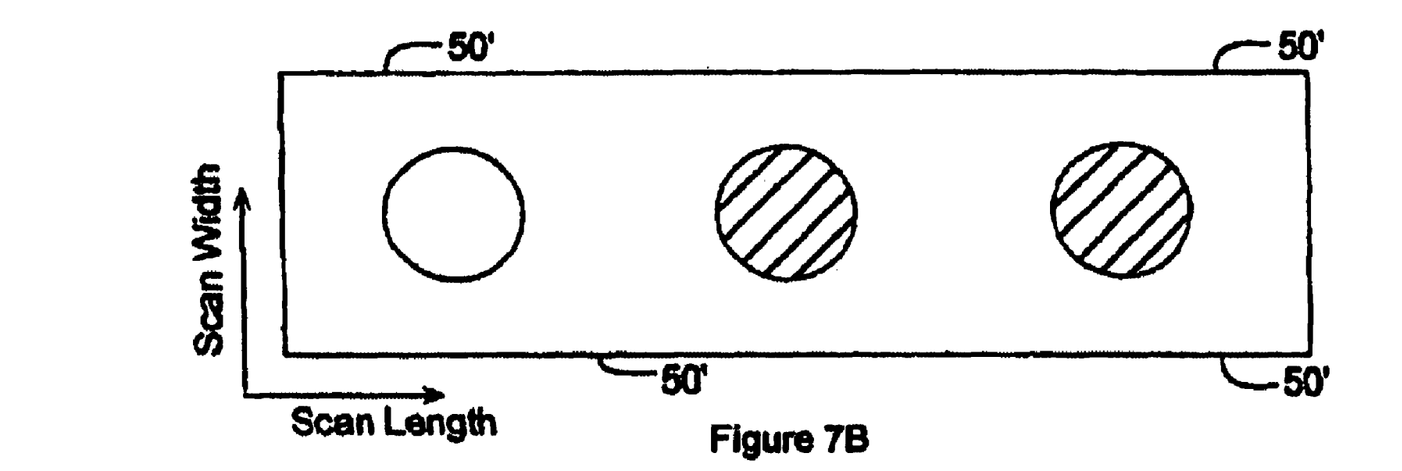
FIG. 7B illustrates typical C-Scans of three sheets welded together to evaluate spot and seam weldments.

FIG. 7B illustrates a plan view image C-Scan 50' (Nondestructive Testing Handbook, Volume II, Edited by the Society for Nondestructive Testing, Ronald Press, NY 1963, pgs 43.34 through 43.36) of the weldments being inspected shown in FIG. 7A. The vertical and horizontal axes of the C-scan image show the scan width and the length of the area scanned (obtained from encoder 20) and include images showing the quality and the location of the ultrasonic reflectors. With this type of image either the amplitude or the time of flight of the signals from the ultrasonic reflectors can be displayed using a color code or a gray scale (shown here for enhanced printability of FIG. 7B as white where there is no weldment or diagonally filled where there is a good weldment beneath the top lay of the component being scanned). The C-scan is especially useful for determining the quality of seam welds by measuring the width and the continuous length of the fusion area.

Figure 8:
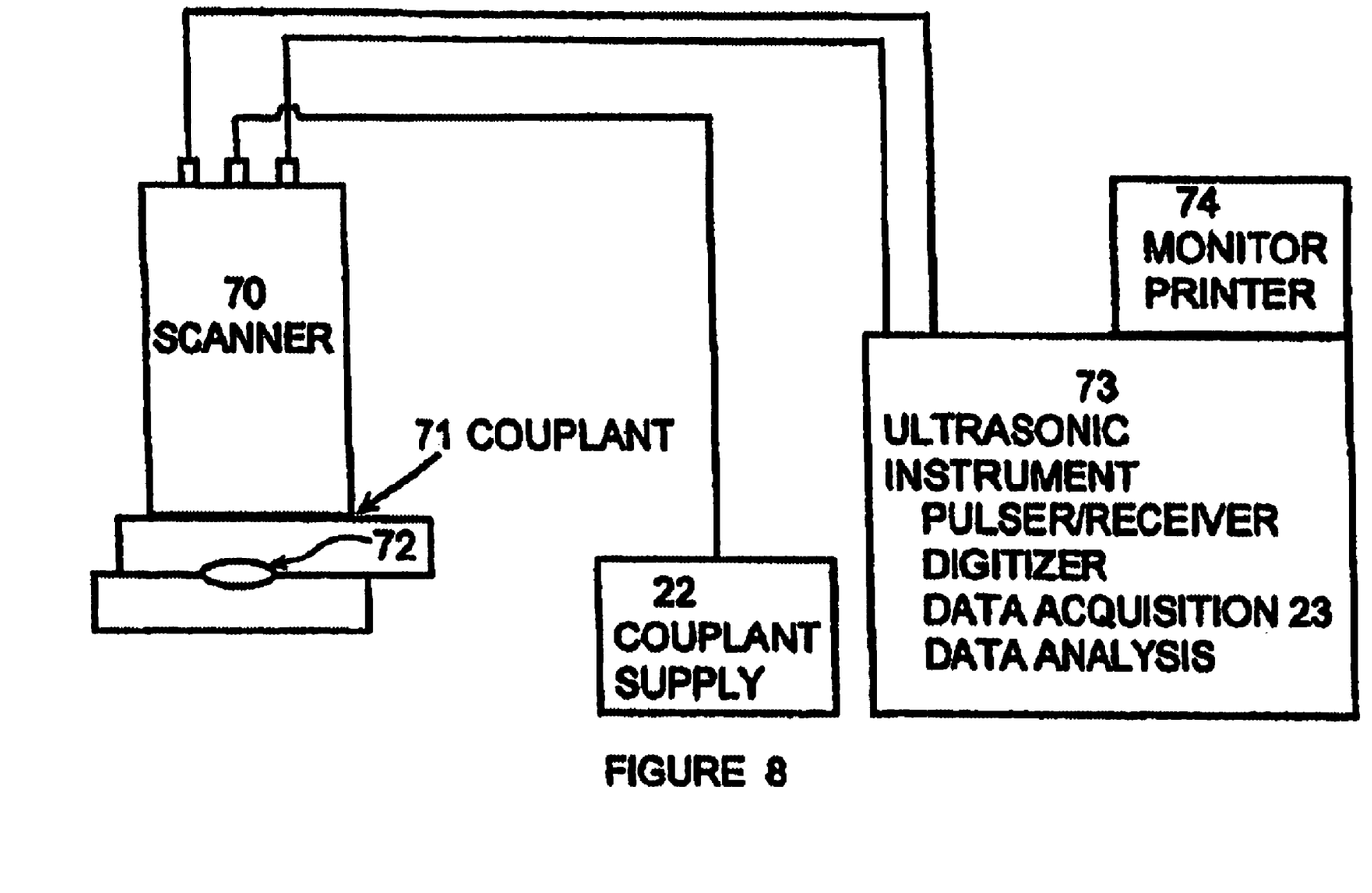
FIG. 8 is a system block diagram of the present invention.

FIG. 8 is a block diagram of the apparatus used for performing the inspections to determine the integrity of weldments and to obtain the dimensional measurements. Scanner 70 includes the items described relative to FIG. 3 with liquid column 25 connected to couplant supply 22 and transducer 11 and encoder 20 providing acquired data to ultrasonic instrument 73 that includes a pulser/receiver, a digitizer, data acquisition unit 23 and a data analysis unit. Attached to ultrasonic instrument 73 are monitor/printer 74. A recording instrument in the form of a printer or magnetic recorder records the A-, B and C-scan images from the monitor to provide a hard copy of the inspection results.

The various elements depicted in the drawings are merely representational and are not drawn to scale. Certain proportions thereof may be exaggerated, while others may be minimized. The drawings are intended to illustrate various implementations of the invention, which can be understood and appropriately carried out by those of ordinary skill in the art.

The many features and advantages of the present invention are apparent from the detailed specification, and, thus, it is intended by the appended claims to cover all such features and advantages of the described apparatus and process that follow the true spirit and scope of the invention. Furthermore, since numerous modifications and changes will readily occur to those of skill in the art, it is not desired to limit the invention to the exact construction and operation described herein. Accordingly, other embodiments are within the scope of the appended claims as well as equivalents thereof.

What is claimed is:

1. A versatile, compact, lightweight ultrasonic probe to inspect a component having spot welds between plates not requiring the immersion of the component in a liquid bath for inspection, comprises:

a housing disposed to be hand held and manually moved along a surface of said component with said housing having a narrow tip disposed to engage said surface of said component to be tested;

a reservoir within said housing disposed to contain and disperse a couplant to said surface of said component as said component is inspected;

an ultrasonic transducer within said housing disposed to direct an ultrasonic signal through said narrow tip and said couplant to said component during inspection and to receive a return signal from said component through said narrow tip and said couplant from said component; and an encoder coupled to said housing and disposed to engage said component to detect a distance of travel of said housing during inspection relative to a reference point on the component.

2. The ultrasonic probe as in claim 1 wherein said encoder includes a traction wheel disposed to contact said component and turn as said housing is moved manually.

3. The ultrasonic probe as in claim 1 wherein said narrow tip of said housing is interchangeable and available in several different sizes to compliment various spot weld sizes.

4. The ultrasonic probe as in claim 1 wherein said encoder and said transducer are each disposed to be coupled to a data acquisition and processing system to processes ultrasonic and distance signals to permit the generation of images from which quality of the spot weld can be determined.

5. The ultrasonic probe of claim 4 wherein the generated images include standard and enhanced A-scan, B-scan and C-scan images.

6. A method of inspection of a component having spot welds between plates without requiring the immersion of the component into a liquid bath for inspection, said method comprising the steps of:

a. engaging a surface of said component with a probe tip attached to a hand held housing;

b. manually advancing said housing over said component with said probe tip engaged with said component;

c. continuously applying and maintaining a couplant between said probe tip and surface of said component;

d. continuously directing an ultrasonic signals through said probe tip and couplant to the surface of said component; and e. continuously detecting signals returned from said component through said couplant and probe tip.

7. The method of inspection as in claim 6 further including the step of:

f. continuously encoding a distance of travel of said probe tip during inspection relative to a reference point on the component.

8. The method of inspection as in claim 7 further including the step of:

g. generating images from which quality of the spot weld can be determined using said detected signal of step e, and said distance of travel of step f.

9. The method of inspection as in claim 8 wherein the generated images include standard and enhanced A-scan, B-scan and C-scan images.

* * * * *